US009089679B2

(12) United States Patent
Fontana

(10) Patent No.: US 9,089,679 B2
(45) Date of Patent: Jul. 28, 2015

(54) DEVICE FOR INTRODUCING SUBSTANCES INSIDE ANIMALS

(75) Inventor: Antonio Fontana, Capri (IT)

(73) Assignee: LAMEPLAST S.P.A., Novi di Modena (MO) (IT)

( * ) Notice: Subject to any disclaimer, the term of this patent is extended or adjusted under 35 U.S.C. 154(b) by 26 days.

(21) Appl. No.: 14/129,372

(22) PCT Filed: Jul. 16, 2012

(86) PCT No.: PCT/IB2012/001385
§ 371 (c)(1),
(2), (4) Date: Dec. 26, 2013

(87) PCT Pub. No.: WO2013/014505
PCT Pub. Date: Jan. 31, 2013

(65) Prior Publication Data
US 2014/0148755 A1    May 29, 2014

(30) Foreign Application Priority Data

Jul. 25, 2011    (IT) .............................. MO2011A0184

(51) Int. Cl.
| A61M 37/00 | (2006.01) |
| A61D 1/02 | (2006.01) |
| A61D 7/00 | (2006.01) |
| A61M 5/315 | (2006.01) |
| A61M 31/00 | (2006.01) |
| A61M 5/46 | (2006.01) |

(52) U.S. Cl.
CPC ........... *A61M 37/0069* (2013.01); *A61D 1/025* (2013.01); *A61D 7/00* (2013.01); *A61M 5/31593* (2013.01); *A61M 5/46* (2013.01); *A61M 31/007* (2013.01)

(58) Field of Classification Search
CPC ..................... A61M 37/0069; A61M 5/31593; A61M 5/46; A61M 31/007; A61D 1/025; A61D 7/00

USPC ......... 604/46–47, 68–72, 131, 140–144, 173, 604/187, 57–64
See application file for complete search history.

(56) References Cited

U.S. PATENT DOCUMENTS

| 4,576,591 A | * | 3/1986 | Kaye et al. ...................... 604/62 |
| 5,106,370 A | * | 4/1992 | Stewart ........................... 604/61 |
| 5,522,797 A | * | 6/1996 | Grimm ............................ 604/61 |
| 5,860,946 A | * | 1/1999 | Hofstatter ....................... 604/15 |
| 6,258,056 B1 | | 7/2001 | Turley et al. | |

FOREIGN PATENT DOCUMENTS

IE             54 832 B1      2/1990

OTHER PUBLICATIONS
International Search Report, dated Sep. 7, 2012, from corresponding PCT application.

* cited by examiner

*Primary Examiner* — Bhisma Mehta
*Assistant Examiner* — Larry R Wilson
(74) *Attorney, Agent, or Firm* — Young & Thompson

(57) ABSTRACT

A device for introducing substances inside animals includes: a base body for housing a cartridge containing a substance in the form of pellets to be introduced into an animal; a hollow needle for penetrating the animal and introducing the substance; a push rod substantially aligned and coaxial with the hollow needle; first operating elements for moving the push rod to push the substance through the hollow needle; a tubular element fitted in the hollow needle and having temporary retention elements for temporarily retaining the substance inside the hollow needle and an open distal extremity of the tubular element, having: first and third segments with constant section, with transversal dimensions substantially equal to those of the tubular element; a second narrowing segment, associated with the first segment and having transversal dimensions at least in part smaller than those of the tubular element.

15 Claims, 11 Drawing Sheets

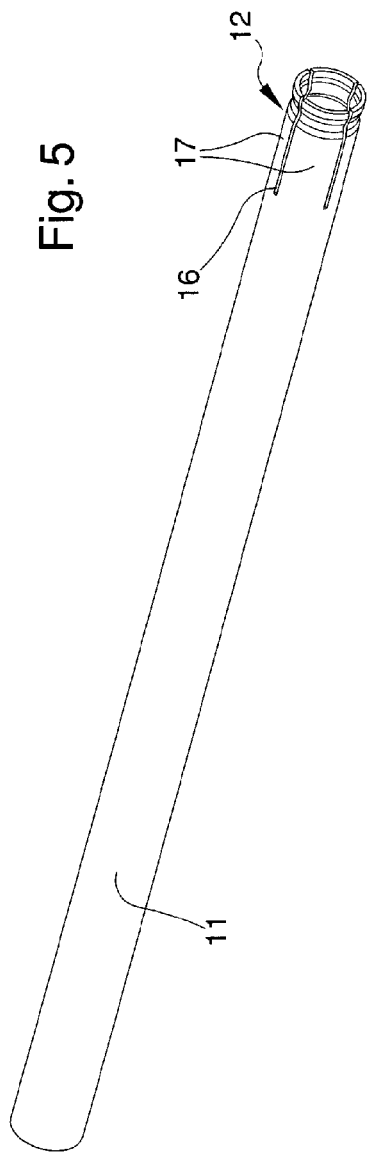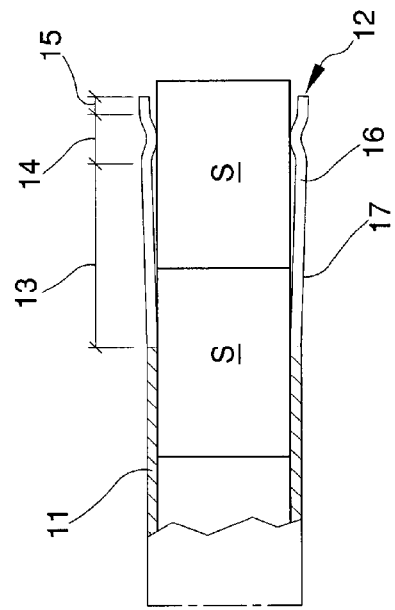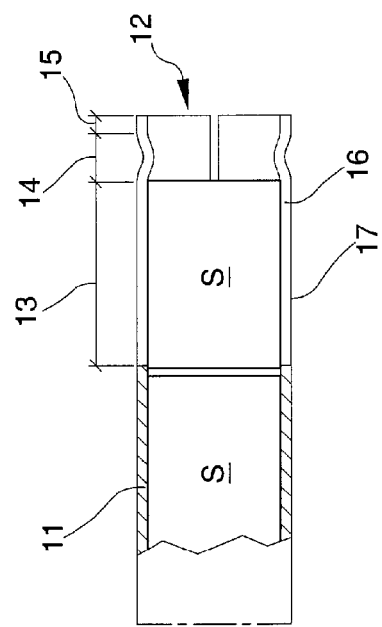

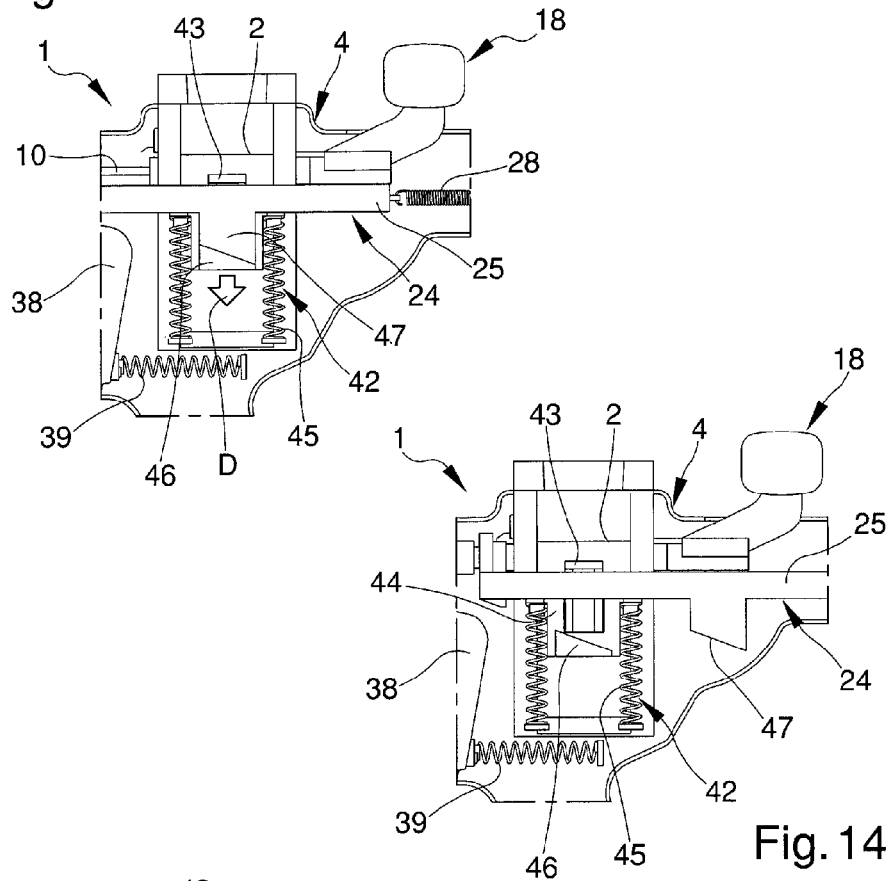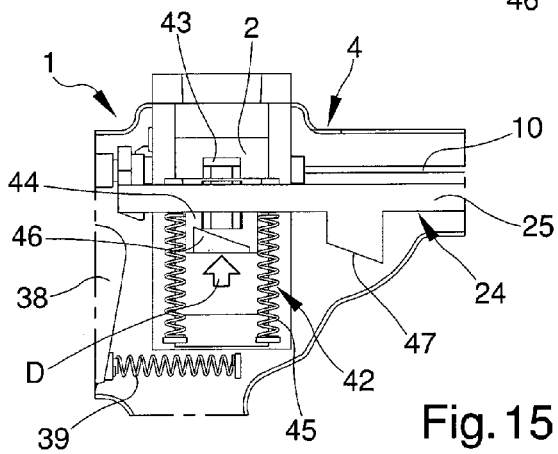

DEVICE FOR INTRODUCING SUBSTANCES INSIDE ANIMALS

TECHNICAL FIELD

The present invention relates to a device for introducing substances inside animals, such as cattle or the like.

BACKGROUND ART

Devices are known having the shape of pistols and made for introducing medicinal substances inside animals.

A particular type of these devices comprises a base body having a handle for gripping by the user.

Inside the base body, a hollow injection needle is fitted, in the proximity of which a cartridge is associable containing one or more doses of medicinal substances in the form of pellets, i.e., small cylindrical capsules, to be introduced into the animal.

The cartridge has a series of cavities containing the pellets and alignable with the hollow needle to be crossed longitudinally by a mobile push rod.

The push rod is fitted on a carriage sliding longitudinally and which can be operated forwards and backwards manually by the user by means of a bayonet mechanism.

The bayonet mechanism appears out of the top of the base body to allow it to be gripped by the user and is connected to the sliding carriage.

By means of the bayonet mechanism, the carriage is made to slide backwards and then forwards.

The forward stroke of the carriage is split into two sections.

During the first section, the hollow needle remains at a standstill while the push rod crosses a cavity of the cartridge and transfers the pellets inside the hollow needle.

During the second section, instead, a push mechanism is triggered that drags forward not only the push rod but also the hollow needle, as far as a blockage position.

At the time of dispensing, the hollow needle is introduced into the animal and, by means of the operation of a release trigger, the hollow needle returns to departure position while the push rod remains at a standstill, ensuring the pellets stay inside the animal and are not dragged by the hollow needle.

Inside the hollow needle, a tubular element is fitted that guides the exit of the pellets and is made to retain these when, once pushed out of the cartridge, they are inside the hollow needle and have to be injected into the animal.

For this purpose, the tubular element has an exit extremity the edge of which is carved and slightly folded towards the inside of the tubular element itself.

The exit extremity made this way therefore has a shape similar to that of a truncated cone.

This device of known type has a number of drawbacks including the fact that the tubular element arranged inside the hollow needle is not able to operate efficiently and reliably for very long.

After being used just a few times in fact, it loses its shape memory and takes on an almost perfectly cylindrical configuration which does not help in any way to retain the pellets inside the hollow needle before these are introduced into the animal.

It often occurs therefore that once the bayonet mechanism has been loaded and the hollow needle has been filled with the pellets to be injected, the latter come out of the hollow needle due to simple gravity.

To overcome this problem, the user is forced to inconveniently always keep the pistol turned upwards, which strongly restricts his/her freedom of movement precisely during the most delicate stage of the operation, i.e., the injection of the hollow needle inside the animal.

To this must be added that the push rod and hollow needle operating system is rather complicated from a constructive and structural viewpoint and very often ends up jamming or producing other operating problems.

Furthermore the use of a bayonet mechanism involves the presence of a gripping knob sliding along the base body and stoppable in an end-of-stroke position, where the gripping knob must be turned on the right side of the pistol.

The gripping knob is therefore very inconvenient to use by left-handed users, which strongly restricts the operating practicality of the entire device.

Another drawback consists in the fact that the device handle, i.e., the butt of the pistol, is located a long way from the hollow needle, i.e., in a particularly retracted position.

Because of this, the manoeuvrability and the stability of the pistol, above all when aiming the hollow needle at the animal and injecting the pellets, is very limited.

Neither should it be forgotten that only one cartridge at a time can be loaded in this pistol, forcing the user to inconveniently have to use a cartridge strap or separate cartridge holder.

This latter drawback is particularly felt in all farms comprising a large number of heads of cattle, where the substances contained in a single cartridge are very quickly finished and where the used cartridges have to be frequently changed with serious loss of time, which inevitably translates into limited productivity and into an inconvenient increase in labour costs.

DESCRIPTION OF THE INVENTION

The main aim of the present invention is to provide a device for introducing substances inside animals which can be used in a practical, easy and functional way with improved efficiency than the traditional devices.

Another object of the present invention is to provide a device for introducing substances inside animals which is not subject to jamming or malfunctioning like the known devices and allows to increase the labour productivity, thus reducing the cost thereof.

Another object of the present invention is to provide a device for introducing substances inside animals which allows to overcome the mentioned drawbacks of the state of the art within the ambit of a simple, rational, easy and effective to use as well as low cost solution.

The above objects are achieved by the present device for introducing substances inside animals, comprising:

at least a base body which can be gripped by a user and having at least a receiving seat suitable for housing at least a cartridge which comprises at least a cavity containing a substance in the form of pellets to be introduced into an animal;

at least a hollow needle suitable for penetrating said animal for the introduction of said substance;

at least a push rod substantially aligned and coaxial with said hollow needle, said cartridge being placeable in a position of use wherein said cavity is placed between said hollow needle and said push rod and is aligned with these;

first operating means suitable for moving said push rod through said cavity in a position of use to push said substance through said hollow needle;

at least a tubular element fitted in said hollow needle and having temporary retention means suitable for temporarily retaining said substance inside said hollow needle;

characterised by the fact that said temporary retention means comprise a distal extremity of said tubular element, which is open and has:
- a first segment with constant section, with transversal dimensions substantially equal to those of said tubular element;
- a second narrowing segment, associated with said first segment and having transversal dimensions at least in part smaller than those of said tubular element;
- a third segment with constant section, associated with said second segment and having dimensions substantially equal to those of said tubular element; and
- a plurality of longitudinal cuts, which extend along said segments and are suitable for dividing said distal extremity into a plurality of longitudinal thin sheets flexible to the outside to allow the compulsory transit of said substance.

BRIEF DESCRIPTION OF THE DRAWINGS

Other characteristics and advantages of the present invention will become more evident from the description of a preferred, but not sole, embodiment of a device for introducing substances inside animals, illustrated purely as an example but not limited to the annexed drawings in which:

FIG. 5 is an axonometric view, on enlarged scale, of a part of the device according to the invention;

FIGS. 6 and 7 are two views in longitudinal section of the part of FIG. 5 which illustrate its operation;

FIGS. 13 to 15 illustrate, in a succession of side, schematic and partial views, the operation of the automatic movement means provided in the device according to the invention.

EMBODIMENTS OF THE INVENTION

Figure 1:
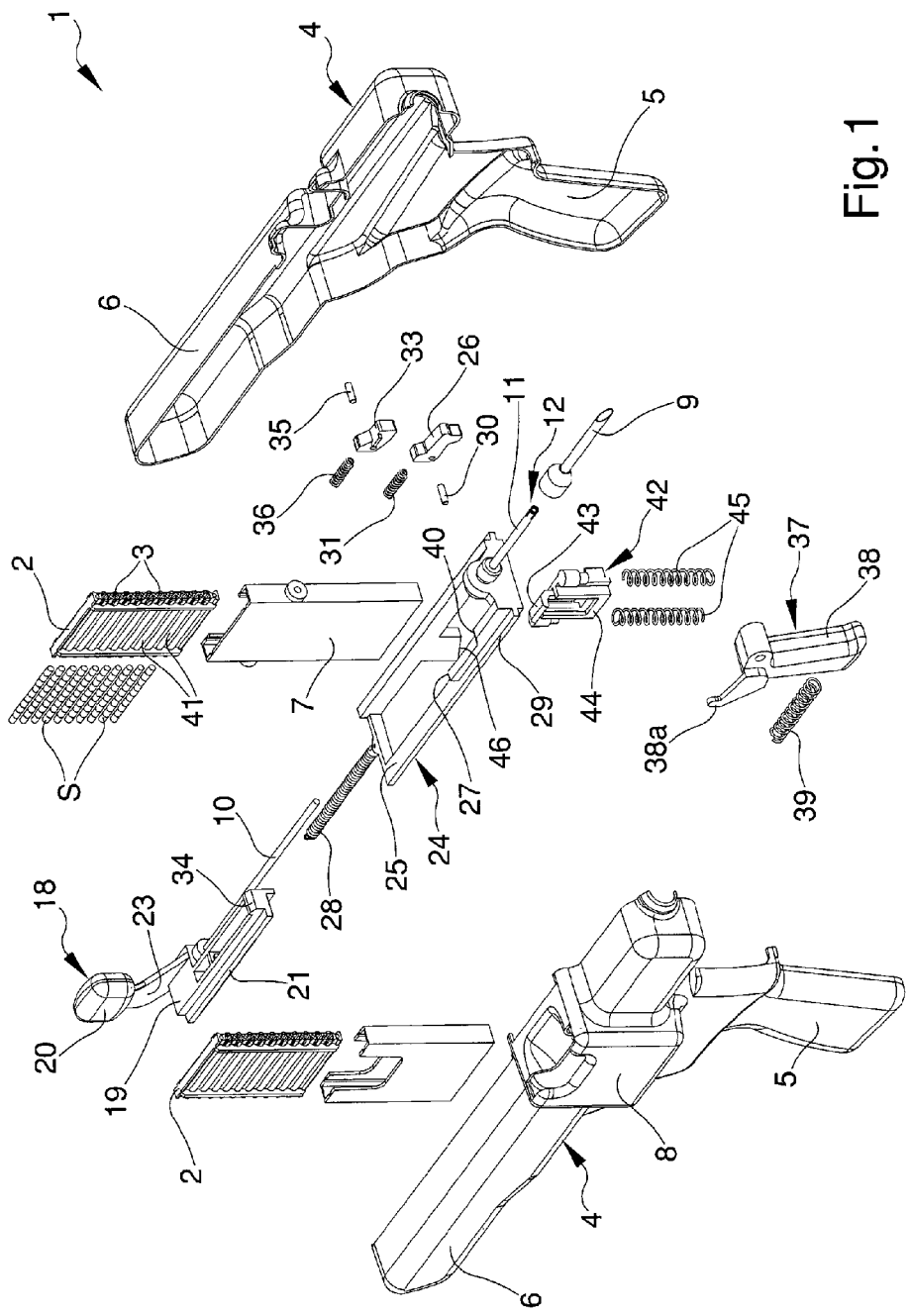
FIG. 1 is an exploded view of the device according to the invention.
Figure 2:
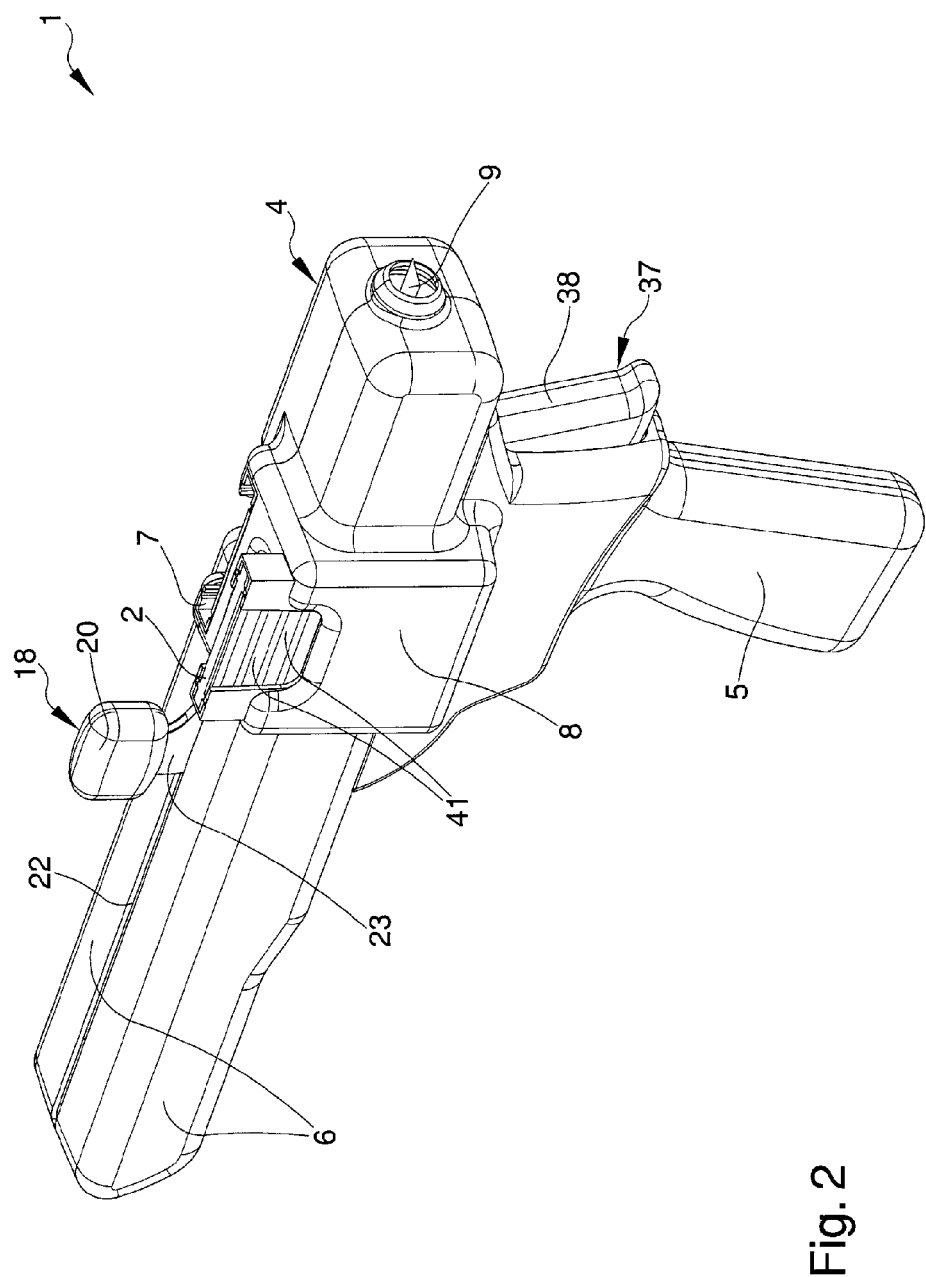
FIG. 2 is an axonometric view of the device according to the invention.
Figure 3:
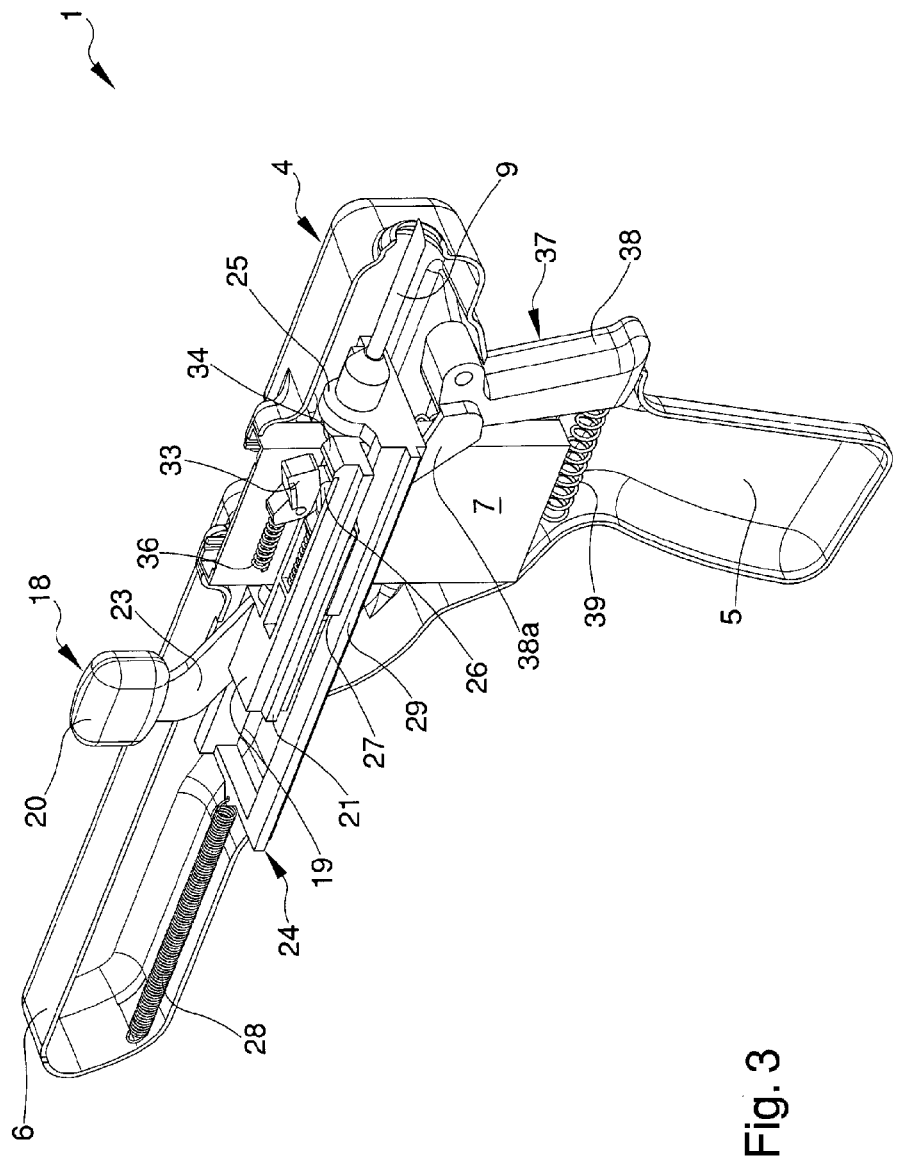
FIG. 3 is an axonometric, partially broken view of the device according to the invention.
Figure 4:
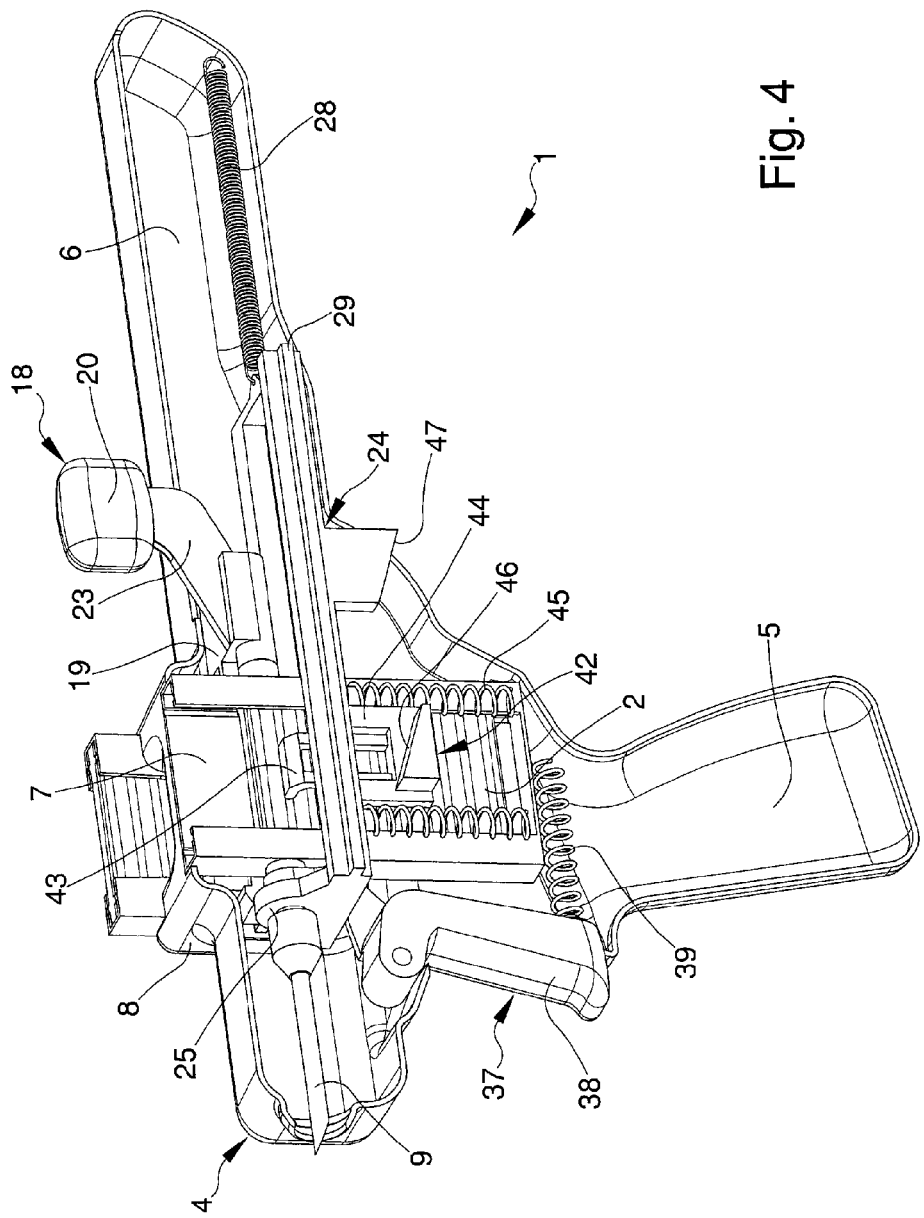
FIG. 4 is an axonometric, partially broken view, from another angle than FIG. 3, of the device according to the invention.

With particular reference to such figures, globally indicated by 1 is a device for introducing substances inside animals The device 1, in particular, is designed for introducing a substance S made in the form of pellets, i.e., small capsules with a substantially cylindrical shape.

The pellets S are contained in a series of cartridges 2, each of which comprises a plurality of cavities 3 containing the pellets S.

The cavities 3 have a cylindrical shape, with constantly round or polygonal cross-section.

The axial extremities of each cavity 3 are open and have one or more flexible teeth for retaining the pellets S; other equivalent retention systems are however possible.

The cartridges 2 have a substantially plate-shaped conformation and the cavities 3 cross them from one side to the other parallel with one of the larger faces of the cartridges 2.

The cavities 3, furthermore, are arranged parallel with one another and spaced out with constant pitch.

The particular shape of the cartridges 2 makes them completely symmetric and specular, both open extremities of the cavities 3 being able to act both as entry opening and as exit opening for the substance S.

Such peculiarity favours the use of the cartridges 2 which, in a practical and easy way can be used indistinctly both in one direction and in the other.

Alternative embodiments cannot however be ruled out wherein the cartridges 2 have a different conformation and, e.g., have just one cavity 3.

The device 1 comprises a base body 4 which is shaped in the form of a pistol and has a handle 5, shaped like the butt of the pistol and which can be ergonomically gripped by a user.

The base body 4 consists, e.g., of two half-shells 6 which can be coupled together.

Once assembled, the base body 4 defines a receiving seat 7 suitable for housing the cartridge 2 being worked.

With reference to the normal gripping position of the base body 4, i.e., with the handle 5 turned downwards, the cartridges 2 can be fitted in the receiving seat 7 with a movement from top to bottom and are removable from bottom to top.

In this respect, it is underlined that in the present treatise the terms "bottom" and "top" are always used with reference to the above-mentioned position of normal gripping of the base body 4.

Alternative embodiments are however possible wherein the loading and unloading of the cartridges 2 occurs along a different direction, e.g., laterally, in which case the terms "bottom" and "top" must be interpreted in a duly adapted way.

Parallel to the receiving seat 7, the base body 4 also has a block 8 for housing another cartridge 2 which remains as a spare.

Alternative embodiments cannot however be ruled out wherein the block 8 is shaped for housing two or more spare cartridges 2.

The device 1 also comprises a hollow needle 9, which is suitable for penetrating the animal A for introducing the substance S and which extends along a longitudinal direction.

In this respect, it is underlined that in the present treatise, the terms "longitudinal" and "transversal" are used with reference to the orientation of the hollow needle 9, which also defines the direction of penetration of the hide of the animal A.

Usefully, the handle 5 of the base body 4 is arranged in the proximity of the hollow needle 9 and, in particular, is positioned substantially below it; such position helps the user to handle the device 1, which in fact can be operated with great stability and precision, in particular as regards the operation of aiming and penetration of the hollow needle 9 into the animal A.

Inside the base body 4 is also housed a push rod 10 substantially aligned and coaxial with the hollow needle 9, the cartridge 2 fitted in the receiving seat 7 being positionable in a sequential way in a position of use wherein each cavity 3 is placed between the hollow needle 9 and the push rod 10 and is aligned with them.

The movement of the push rod 10 in longitudinal direction allows pushing the substance S along the cavity 3 and right inside the hollow needle 9 or, more correctly, inside a tubular element 11 substantially housed to measure inside the hollow needle 9.

The tubular element 11 has temporary retention means 12 suitable for temporarily retaining the substance S inside the hollow needle 9.

The temporary retention means 12 consist in a distal extremity of the tubular element 11, which is open to allow the transit of the pellets S and has:

a first segment 13 with constant section, having transversal dimensions substantially equal to those of the tubular element 11;

a second narrowing segment 14 associated with the first segment 13 and having transversal dimensions at least in part smaller than those of the tubular element 11;

a third segment 15 with constant section associated with the second segment 14 and having dimensions substantially equal to those of the tubular element 11; and a plurality of longitudinal cuts 16 which extend along the segments 13, 14, 15 and are suitable for dividing the distal extremity 12 into a plurality of longitudinal thin sheets 17 flexible to the outside to allow the compulsory transit of the substance S.

In this respect, it is underlined that by "transversal dimensions" of the three segments 13, 14, 15 is meant the overall dimensions which the three segments have along a transversal direction.

The first segment 13 and the third segment 15 therefore have a substantially cylindrical shape with diameter equal to that of the tubular element 11.

The second segment 14, on the other hand, has a concave toroid shape and, in longitudinal section, has a substantially curvilinear profile extending in centripetal direction towards the central axis of the tubular element 11.

In other words, the narrowing meant to retain the pellets S is obtained on the second segment 14 and not in correspondence to the exit opening of the distal extremity 12, corresponding to the third segment 15 which, as has been said, has an overall transversal dimension equal to that of the tubular element 11.

This particular shape allows obtaining the distal extremity 12 starting with a tubular element 11 without longitudinal cuts 16 and perfectly cylindrical, submitting it to:

a first operation of "rolling for forming an internal overhanging groove", which impresses the shape on the second segment 14;

a subsequent "incision" operation, which allows obtaining the longitudinal cuts 16 and defining the longitudinal thin sheets 17.

In this respect, it is underlined that the deformation and the shaping of the second segment 14 does not occur in correspondence to the exit opening (i.e. the third segment 15), which instead remains perfectly integral and able to withstand the mechanical forces produced by the rolling of the second segment 14.

The material making up the distal extremity 12, therefore, undergoes less tensioning stresses and, once cut to define the longitudinal thin sheets 17, is able to maintain its elastic memory needed for the correct operation of the distal extremity 12.

Also provided are first operating means 18 suitable for moving the push rod 10 longitudinally through the cavity 3 which is located in a position of use, so as to push the substance S contained in it through the hollow needle 9 and therefore into the animal A.

The first operating means 18 comprise:

a first carriage 19 supporting the push rod 10 and mounted inside the base body 4 in a longitudinally sliding way, and a gripping knob 20, associated with the first carriage 19 and which can be gripped by a user for dragging the first carriage 19 between a first retracted position, wherein the push rod 10 is external to the cavity 3, a first intermediate position, wherein the push rod 10 is fitted in the cavity 3 and the substance S is completely pushed inside the hollow needle 9, and a first forward position, wherein the push rod 10 is further fitted into the cavity 3.

In particular, the first carriage 19 has first ribbings 21 engageable along corresponding first guide grooves obtained inside the base body 4.

For simpler representation, the first guide grooves are not shown in the illustrations while the first ribbings 21 are only shown in some of them.

The half-shells 6 are shaped so as to define a longitudinal guide slot 22 in correspondence to their joining plane.

The longitudinal guide slot 22 is crossed by an upright 23 which connects the first carriage 19, arranged inside the base body 4, and the gripping knob 20, arranged external to the base body 4.

The longitudinal guide slot 22 and the gripping knob 20 are arranged on the surface of the base body 4 which is turned upwards, even though alternative solutions cannot be ruled out wherein, instead, these are located underneath or at the side.

The location of the gripping knob 20 above the base body 4, and the fact that it can be operated along a longitudinal direction only, means that the device 1 can be freely used either gripping it with the right hand or gripping it with the left hand.

Advantageously, the device 1 also comprises second operating means 24 suitable for moving the hollow needle 9, and the corresponding tubular element 11 housed inside it, with respect to the base body 4.

The second operating means 24 comprise:

a second carriage 25 supporting both the hollow needle 9 and the tubular element 11 and associated with the base body 4 in a longitudinally sliding way;

a stop element 26, mounted on the first carriage 19 and suitable for coming into contact with the reference edge 27 obtained on the second carriage 25 and for pushing it from a second retracted position, wherein the hollow needle 9 is arranged in the proximity of the cavity 3, to a second forward position, wherein the hollow needle 9 is moved away from the cavity 3; and an elastic return element 28 suitable for contrasting the sliding of the second carriage 25 from the second retracted position to the second forward position.

In particular, the second carriage 25 has second ribbings 29 engageable along corresponding second guide grooves obtained inside the base body 4.

As in the case of the first carriage 19, the second guide grooves are not shown in the illustrations and the second ribbings 29 are shown only in some of them for the sake of simpler representation.

The stop element 26 is mounted on the first carriage 19 in a way swinging around a first swinging pin 30 substantially transversal and in contrast with a first return spring 31.

The stop element 26 is suitable for coining into contact with the reference edge 27 when the first carriage 19 reaches the first intermediate position and the second carriage 25 is in the second retracted position.

Consequently, the movement of the first carriage 19 from the first intermediate position to the first forward position corresponds to the movement of the second carriage 25 from the second retracted position to the second forward position.

This means that during the last forward movement stage of the gripping knob 20, the push rod 10 and the hollow needle 9 move forward together in an integral way.

The elastic return element 28 consists, e.g., of a helical spring operating in traction, the extremities of which are associated with the second carriage 25 and with a pin 32 associated with one of the half-shells 6.

Usefully, the device 1 comprises temporary locking means 33, 34 suitable for temporarily retaining the first carriage 19 in the first forward position and the second carriage in the second forward position.

The temporary locking means 33, 34 comprise a skip element 33, which is associated with the base body 4 in a swinging way around a second swinging pin 35 in contrast to a second return spring 36 and is engageable by skipping on a toothed profile 34 obtained on the first carriage 19.

The locking of the first carriage 19 by means of the skip element 33 is enough to also retain the second carriage 25.

The second carriage 25, does in fact remain locked in the second forward position due to the stop element 26 which pushes on the reference edge 27 and prevents the return of the second carriage 25 to the second retracted position.

To release the second carriage 25 from the first carriage 19 a release apparatus 37 is provided suitable for allowing the return of the second carriage 25 from the second forward position to the second retracted position due to the action of the elastic return element 28.

The release apparatus 37 comprises a lever 38 which can be operated by the user and which is associated with the base body 4 in a movable way between a configuration away from the stop element 26 and a configuration near the stop element, wherein the lever 38 moves the stop element 26 away from the reference edge 27, releasing the second carriage 25.

The lever 38, in particular, is hinged to the base body 4 in the proximity of the handle 5 and acts as the trigger of the pistol.

The lever 38 is located up fast against a thrust bearing spring 39, which returns the lever 38 to its original position once it has been released by the user.

The lever 38 also has an appendix 38a which extends inside the base body 4 and which, in the near configuration, is meant to press on the stop element 26 to make it rotate around the first swinging pin 30.

To release the first carriage 19 from the temporary locking means 33, 34, on the other hand, a release mechanism 40 is provided suitable for releasing the first carriage 19 and allowing it to move from the first forward position to the first retracted position.

The release mechanism 40 consists, e.g., of a ramp-shaped profile obtained on the second carriage 25 and suitable for engaging the stop element 26 during the return of the second carriage 25 from the second forward position to the second retracted position.

The ramp-shaped profile 40 pushes the stop element 26 causing it to turn around the first swinging pin 30 and to push against the skip element 33 which thus moves away from the toothed profile 34 and releases the first carriage 19.

Inside the receiving seat 7 the cartridges 2 are sliding along a sliding direction D substantially crossways to the hollow needle 9 to place the cavities 3 in succession in the position of use.

For this purpose each cartridge 2 has a succession of grip teeth 41 engageable by automatic movement means 42 suitable for moving the cartridge 2 in the receiving seat 7 at each cycle of use to place a different cavity 3 in the position of use.

In detail, the automatic movement means 42 comprise a fastening element 43 which, due to the movement of the second carriage 25 which supports the hollow needle 9, is mobile with reciprocating motion along the sliding direction D.

The fastening element 43 is suitable for:
  skip fastening the grip teeth 41 when the push rod 10 is fitted into one of the cavities 3 (first intermediate or forward position of the first carriage 19) to stop the cartridge 2 from sliding, and
  dragging the cartridge 2 along the sliding direction D when the push rod 10 is outside the cavity 3 (first retracted position of the first carriage 19).

More in detail, the fastening element 43 is arranged on one side of the receiving seat 7 on the opposite side to the skip element 33.

The fastening element 43 consists, e.g., of a tooth that can be snap engaged with the grip teeth 41 and mounted on a bracket 44.

The bracket 44 is sliding along the receiving seat 7 in contrast to an elastic return system 45 made up, e.g., of one or more springs placed between the bracket 44 and the base body 4.

The bracket 44, furthermore, has a cuneiform body 46 engageable by a corresponding tilted table 47 associated with the second carriage 25.

When the second carriage 25 is arranged in the second forward position, the tilted table 47 engages the cuneiform body 46 and pushes the bracket 44 downwards, compressing the elastic return system 45 and moving the fastening element 43 to skip engage the next grip tooth 41.

When the second carriage 25 is arranged in the second retracted position, on the other hand, the tilted table 47 is distant from the cuneiform body 46 and the elastic return system 45 pushes the bracket 44 upwards; in the event of the push rod 10 being fitted in one of the cavities 3, then the bracket 44 remains at a standstill, while in the event of the push rod 10 being extracted from the cavities 3, then the bracket 44 is pushed upwards, also dragging with it the cartridge 2. The device 1 operates as follows.

With the first carriage 19 arranged in the first retracted position, the cartridge 2 containing the pellets S to be introduced into the animal A is pushed manually by the user inside the receiving seat 7.

Figure 8:
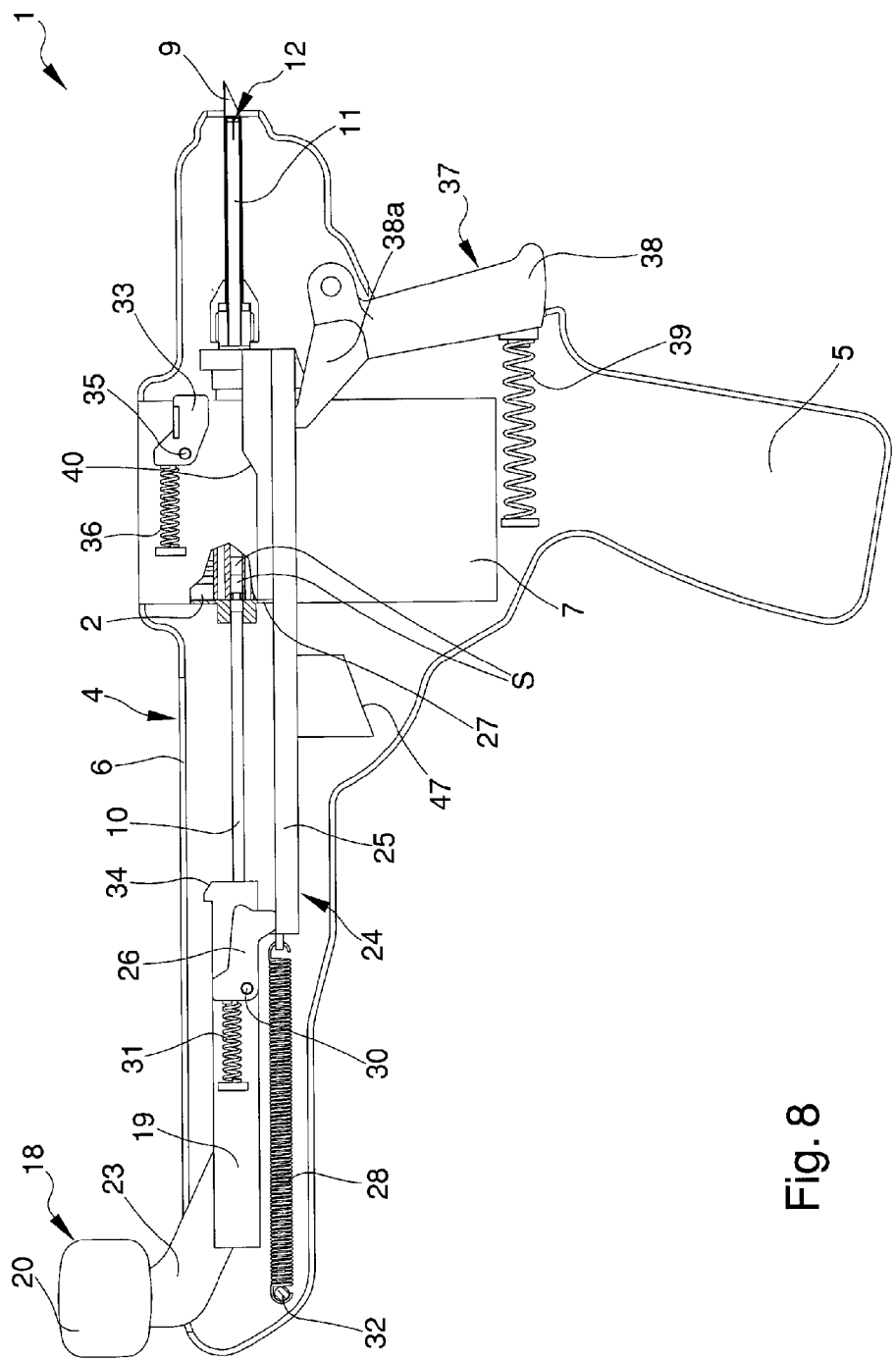
FIGS. 8 to 12 illustrate, in a succession of side views in partial transparency, the operation of the device according to the invention.

This introduction occurs from top downwards until the fastening element 43 has fastened onto the first grip tooth 41 of the cartridge 2, i.e., that arranged higher up, leaving one of the cavities 3 in position of use (FIG. 8).

In this configuration, the second carriage 25 is retained in the second retracted position by means of the elastic return element 28 and, consequently, the hollow needle 9 is arranged in the proximity of the cavity 3.

At this point, the user pushes the gripping knob 20 forward along the longitudinal guide slot 22 causing the first carriage 19 to move forward and introducing the push rod inside the cavity 3.

This determines the transfer of the pellets S from the cavity 3 to the hollow needle 9 and, more in detail, to the tubular element 11 contained in the hollow needle 9.

Figure 9:
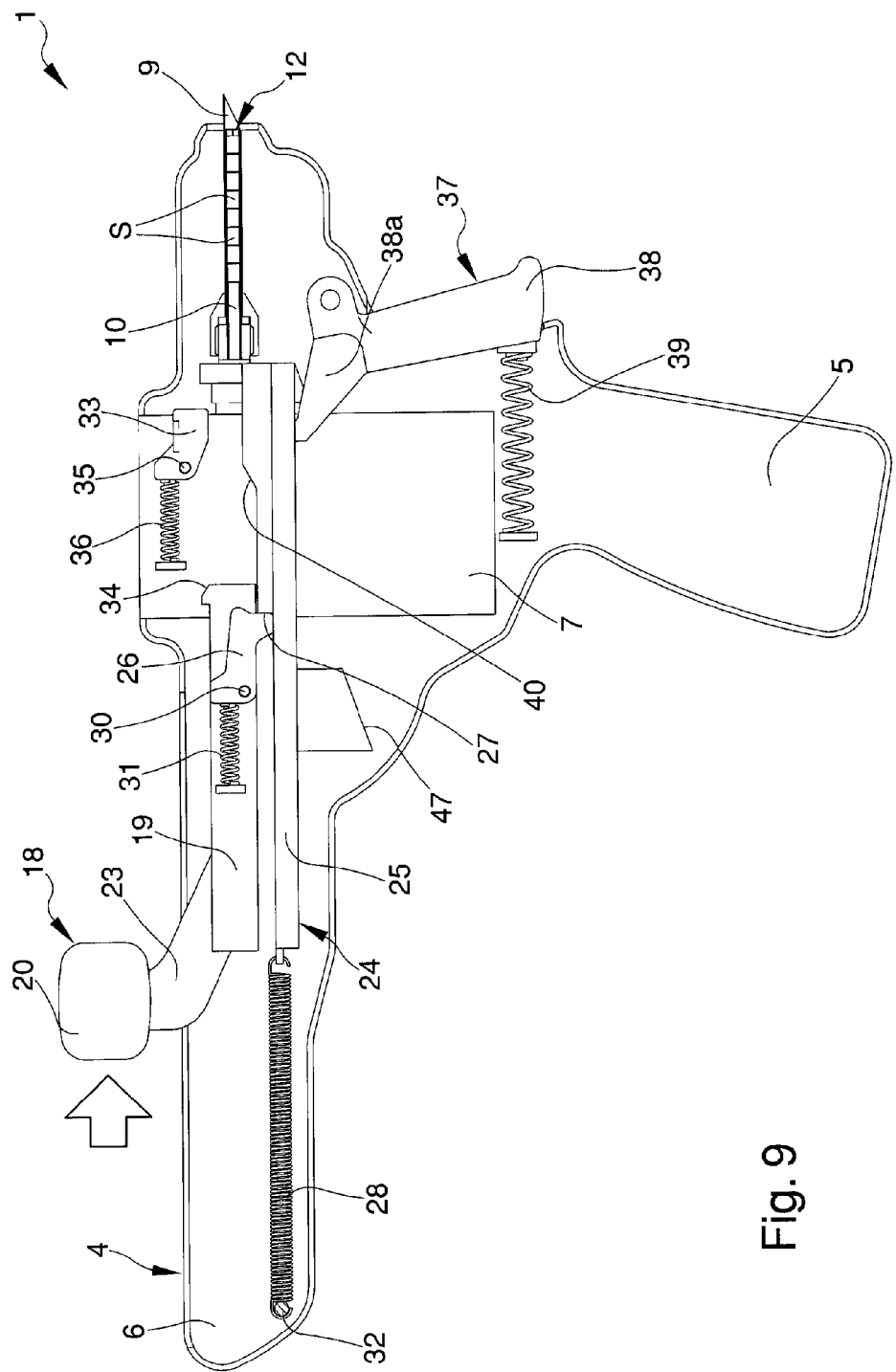

After reaching the first intermediate position, the pellets S are all transferred inside the hollow needle 9 and the stop element 26 comes into contact with the reference edge 27 of the second carriage 25 (FIG. 9).

Figure 10:
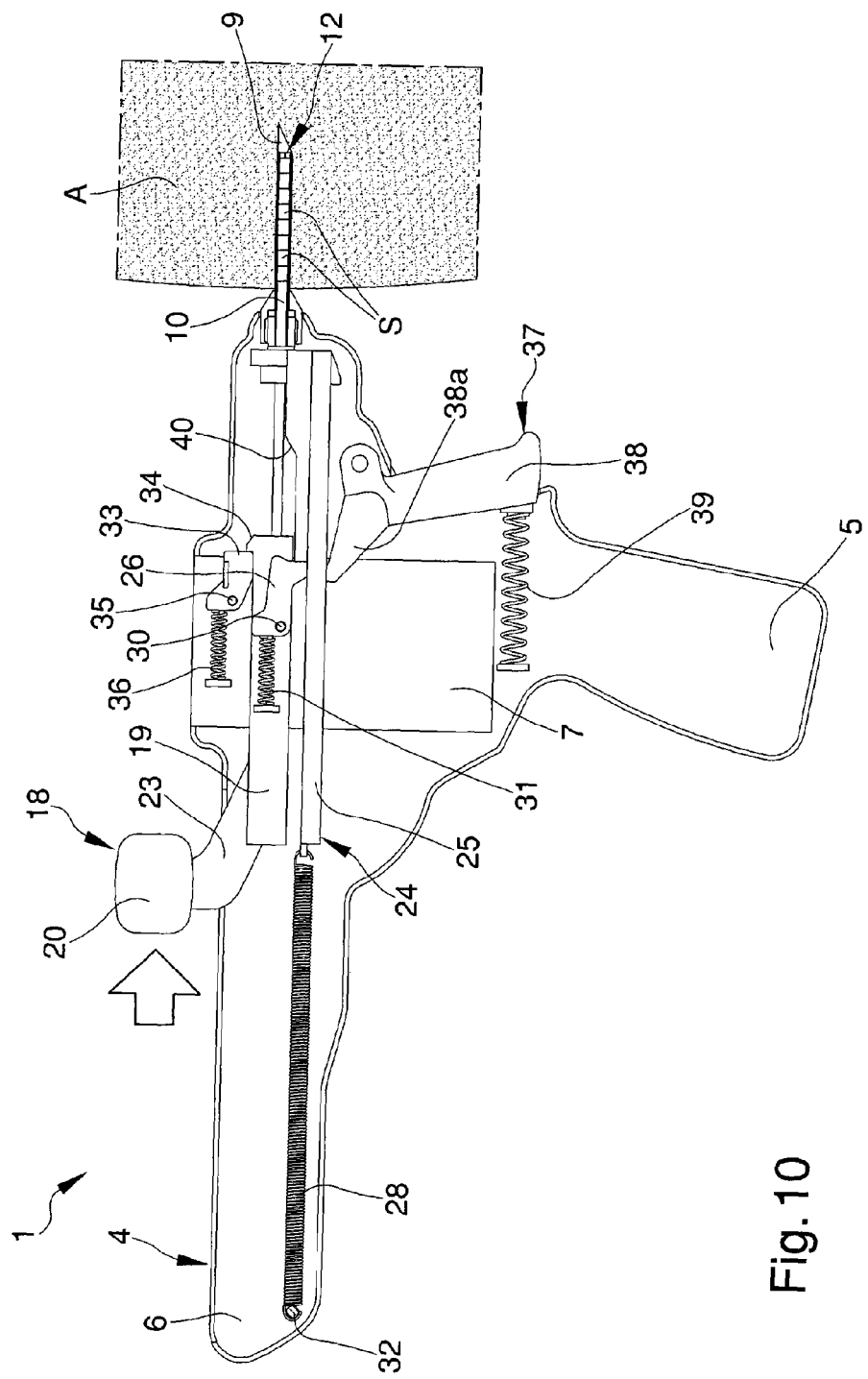

By continuing to move the gripping knob 20 forward, the user, with just one movement, is able to move at the same time both the first carriage 19, which switches from the first intermediate position to the first forward position, and the second carriage 25, which switches from the second retracted position to the second forward position (FIG. 10).

In this configuration, the toothed profile 34 of the first carriage 19 ends its stroke by engaging with the skip element 33, which retains it, blocking both the first carriage 19 and the second carriage 25.

At the same time, the forward movement of the second carriage 25 moves the tilted table 47 closer to the cuneiform body 46, determining the lowering of the bracket 44 along the receiving seat 7.

During such lowering the following occurs:
the cartridge 2 remains blocked by the push rod 10, which is fitted in one of its cavities 3 preventing it from sliding;
the fastening element 43 skip engages the following grip tooth 41;
the elastic return system 45 is compressed (FIG. 13).

The device 1 is therefore ready to be introduced inside the animal A.

During such operation, the user exploits the possibility of freely handling the device 1 without any fear of the pellets S coming out of the hollow needle 9. The particular shape of the distal extremity 12, in fact, retains the pellets S and prevents them coming out even in the case of the device 1 being arranged with the hollow needle 9 turned downwards.

Once the hollow needle 9 has been introduced inside the animal A, the operation of the lever 38 determines the swinging of the stop element 26 and the release of the second carriage 25, which is straight away dragged by the elastic return element 28.

Figure 11:
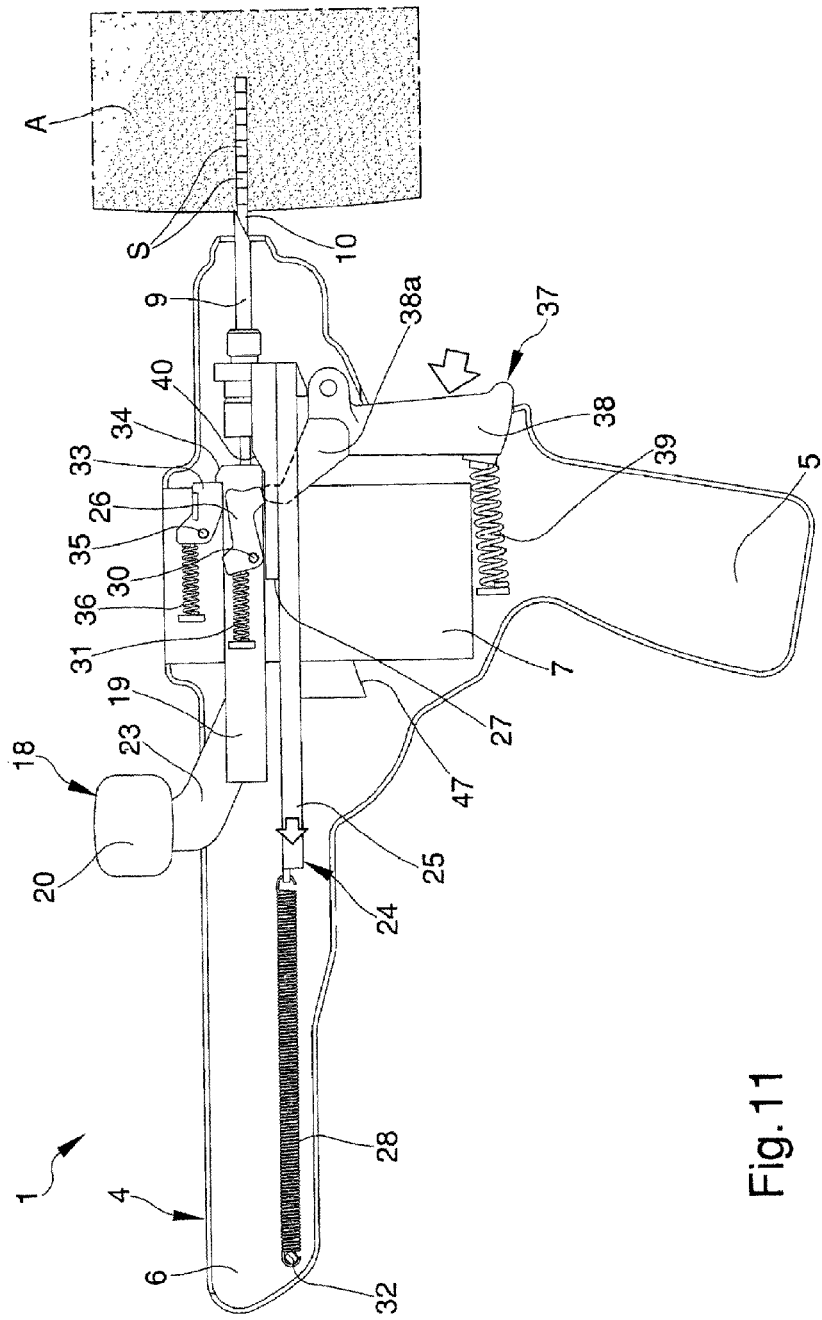

The return of the second carriage 25 towards the second retracted position drags out of the animal A both the hollow needle 9 and the tubular element 11 contained in it, while the push rod 10 remains still and keeps the pellets S inside the animal A (FIG. 11).

Figure 12:
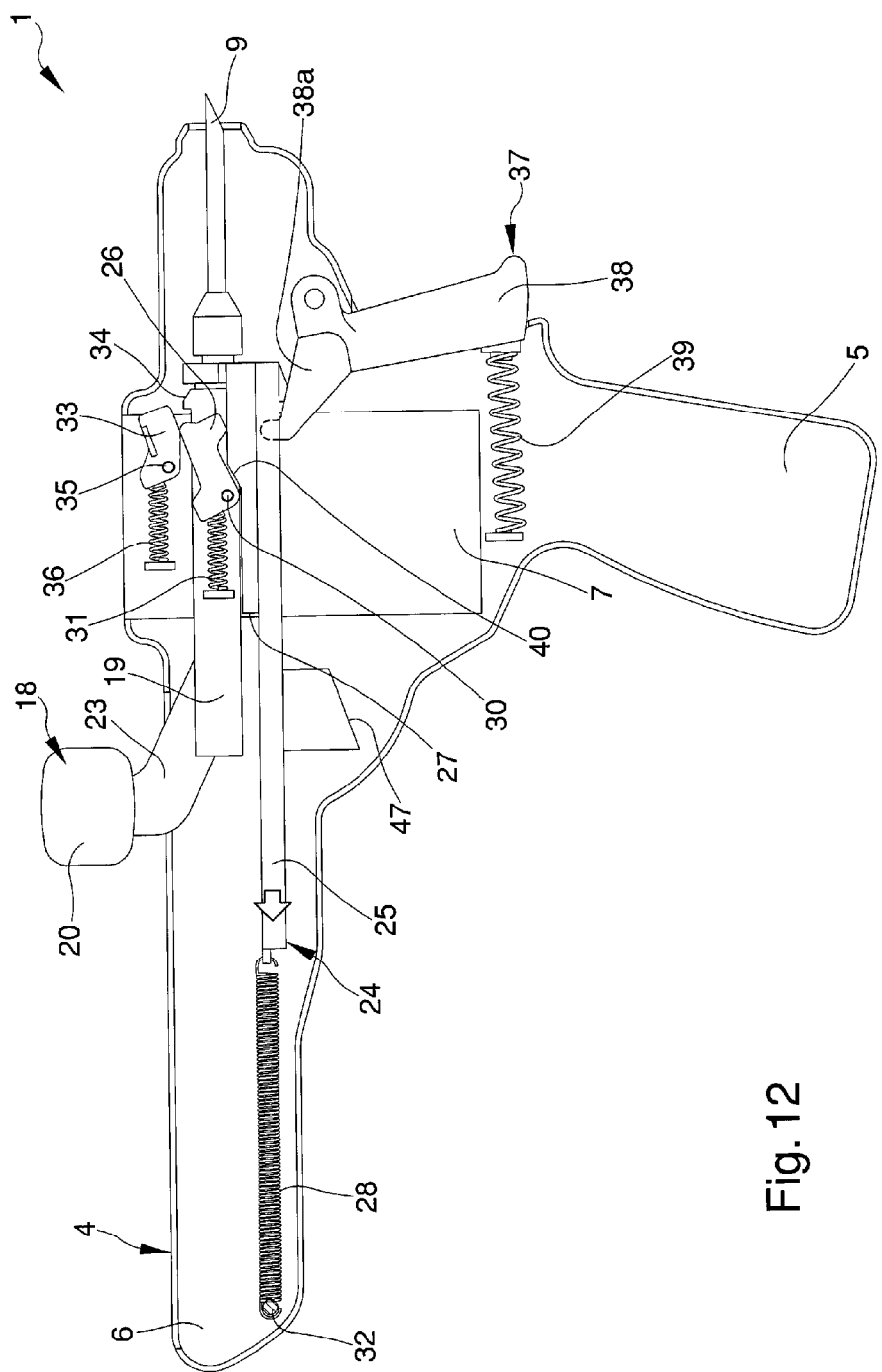

During the return of the second carriage 25 from the second forward position to the second retracted position, the ramp-shaped profile 40 comes into contact with the stop element 26 and pushes this upwards against the skip element 33, releasing the toothed profile 34 and the first carriage 19 (FIG. 12).

At this moment, the tilted table 47 is positioned away from the cuneiform body 46 and the springs 45 placed between the bracket 44 and the base body 4 are still compressed by the previous loading exercised by the cuneiform body 46. The bracket 44 and the cartridge 2, however, do not change their position inasmuch as the push rod 10 is still fitted in the cavity 3 (FIG. 14).

At the next operating cycle, the user makes the push rod 10 reverse again, moving the first carriage 19 from the first forward position to the first retracted position.

In this position, the push rod 10 releases the cartridge 2, which is straight away pushed upwards and moves a new cavity 3 to a position of use, making the pellets S inside it available for introduction into another animal A (FIG. 15). Once all the cavities 3 have been emptied, the cartridge 2 is expelled from the last release of the bracket 44 and is picked up by the receiving seat 7 to be replaced by another.

The invention claimed is:

1. A device (1) for introducing substances (S) inside animals (A), comprising:
at least a base body (4) which can be gripped by a user and having at least a receiving seat (7) adapted for housing at least a cartridge (2) which comprises at least a cavity (3) containing a substance (S) in the form of pellets to be introduced into an animal (A);
at least a hollow needle (9) adapted for penetrating said animal (A) for the introduction of said substance (S);
at least a push rod (10) substantially aligned and coaxial with said hollow needle (9), said cartridge (2) being placeable in a position of use wherein said cavity (3) is placed between said hollow needle (9) and said push rod (10) and is aligned with the hollow needle and the push rod;
first operating means (18) suitable for moving said push rod (10) through said cavity (3) in a position of use to push said substance (S) through said hollow needle (9); and
at least a tubular element (11) fitted in said hollow needle (9) and having temporary retention means (12) suitable for temporarily retaining said substance (S) inside said hollow needle (9),
wherein said temporary retention means (12) comprise a distal extremity of said tubular element (11), which is open and has:
a first segment (13) with constant section, with transversal dimensions substantially equal to those of said tubular element (11);
a second narrowing segment (14), associated with said first segment (13) and having transversal dimensions at least in part smaller than those of said tubular element (11);
a third segment (15) with constant section, associated with said second segment (14) and having dimensions substantially equal to those of said tubular element (11); and
a plurality of longitudinal cuts (16), which extend along said segments (13, 14, 15) and are adapted for dividing said distal extremity (12) into a plurality of longitudinal thin sheets (17) flexible to an outside to allow compulsory transit of said substance (S),
wherein said first operating means (18) comprise:
at least a first carriage (19) supporting said push rod (10) and associated with said base body (4) in a longitudinally sliding way; and
at least a gripping knob (20), associated with said first carriage (19) and which can be gripped by a user for dragging said first carriage (19) between a first retracted position, wherein said push rod (10) is external to said cavity (3), a first intermediate position, wherein said push rod (10) is fitted in said cavity (3) and said substance (S) is completely pushed inside said hollow needle (9), and a first forward position, wherein said push rod (10) is further fitted into said cavity (3),
wherein said device (1) further comprises second operating means (24) suitable for moving said hollow needle (9) with respect to said base body (4) and wherein said second operating means (24) comprise:
at least a second carriage (25) supporting said hollow needle (9) and associated with said base body (4) in a longitudinally sliding way; and
at least a stop element (26), mounted on said first carriage (19) and adapted for coming into contact with a reference edge (27) of said second carriage (25) and pushing it from a second retracted position, wherein said hollow needle (9) is arranged in a proximity of said cavity (3), to a second forward position, wherein said hollow needle (9) is moved away from said cavity (3), and
wherein said device (1) further comprises temporary locking means (33, 34) suitable for temporarily retaining said first carriage (19) in said first forward position and said second carriage (25) in said second forward position.

2. The device (1) according to the claim 1, wherein, in a longitudinal section, said second segment (14) has a substantially curvilinear profile.

3. The device (1) according to the claim 1, wherein said gripping knob (20) is arranged on a surface of said base body (4) which is turned upwards.

4. The device (1) according to claim 1, wherein said device (1) comprises second operating means (24) suitable for moving said hollow needle (9) with respect to said base body (4).

5. The device (1) according to the claim 1, wherein said stop element (26) is adapted for coming into contact with said reference edge (27) when said first carriage (19) reaches said first intermediate position and said second carriage (25) is in said second retracted position, a movement of said first carriage (19) from said first intermediate position to said first forward position corresponding to a movement of said second carriage (25) from said second retracted position to said second forward position.

6. The device (1) according to the claim 1, wherein said second operating means (24) comprise at least an elastic return element (28) adapted for contrasting a sliding of said second carriage (25) from said second retracted position to said second forward position.

7. The device (1) according to the claim 1, wherein said temporary locking means (33, 34) comprise at least a skip element (33) associated with said base body (4) and engageable by skipping on a toothed profile (34) of said first carriage (19), said second carriage (25) remaining locked in said second forward position due to said stop element (26).

8. The device (1) according to claim 7, wherein said device (1) comprises at least a release mechanism (40) for releasing said first carriage (19) from said temporary locking means (33, 34) suitable for allowing a movement of said first carriage (19) from said first forward position to said first retracted position.

9. The device(1) according to the claim 8, wherein said release mechanism (40) comprises a ramp-shaped profile obtained on said second carriage (25) and suitable for engaging said stop element (26) during a return of said second carriage (25) from said second forward position to said second retracted position, said ramp-shaped profile (40) pushing said stop element (26) against said skip element (33) to move said skip element (33) away from said toothed profile (34).

10. The device (1) according to claim 1, wherein said device (1) comprises at least a release apparatus (37) for releasing said second carriage (25) from said first carriage (19) adapted for allowing a return of said second carriage (25) from said second forward position to said second retracted position due to an elastic return element (28).

11. The device (1) according to the claim 10, wherein said release apparatus (37) comprises at least a lever (38) which can be operated by a user and associated with said base body (4) in a movable way between a configuration away from said stop element (26) and a configuration near said stop element (26), wherein said lever (38) moves said stop element (26) away from said reference edge (27).

12. The device (1) according to claim 1, wherein said cartridge (2) comprises a plurality of said cavities (3) and is sliding in said receiving seat (7) along a sliding direction (D) substantially crossways to said hollow needle (9) to place in succession said cavities (3) in said position of use.

13. The device (1) according to the claim 12, wherein said cartridge (2) has a succession of grip teeth (41) engageable by automatic movement means (42) suitable for moving said cartridge (2) at each cycle of use to place one of said cavities (3) in said position of use.

14. The device (1) according to the claim 13, wherein said automatic movement means (42) comprise:
at least a fastening element (43) which, due to a movement of said hollow needle (9), is mobile with reciprocating motion along said sliding direction (D) and is adapted for:
skip fastening said grip teeth (41) when said push rod (10) is fitted in one of said cavities (3) to stop the sliding of said cartridge (2), and for
dragging said cartridge (2) along said sliding direction (D) when said push rod (10) is outside said cavities (3).

15. The device (1) according to claim 1, wherein said base body (4) comprises a handle (5) arranged in a proximity of said hollow needle (9).

\* \* \* \* \*